US012383727B2

(12) United States Patent
Kassel et al.

(10) Patent No.: US 12,383,727 B2
(45) Date of Patent: Aug. 12, 2025

(54) MOTOR HOUSING MODULE FOR A HEART SUPPORT SYSTEM, AND HEART SUPPORT SYSTEM AND METHOD FOR MOUNTING A HEART SUPPORT SYSTEM

(71) Applicant: KARDION GMBH, Stuttgart (DE)

(72) Inventors: Julian Kassel, Böblingen (DE); David Minzenmay, Stuttgart (DE); Thomas Alexander Schlebusch, Renningen (DE)

(73) Assignee: Kardion GmbH, Stuttgart (DE)

( * ) Notice: Subject to any disclaimer, the term of this patent is extended or adjusted under 35 U.S.C. 154(b) by 1039 days.

(21) Appl. No.: 17/057,243

(22) PCT Filed: May 30, 2019

(86) PCT No.: PCT/EP2019/064156
§ 371 (c)(1),
(2) Date: Jun. 22, 2021

(87) PCT Pub. No.: WO2019/229222
PCT Pub. Date: Dec. 5, 2019

(65) Prior Publication Data
US 2021/0316133 A1 Oct. 14, 2021

(30) Foreign Application Priority Data
May 30, 2018 (DE) .................. 102018208539.0

(51) Int. Cl.
*A61M 60/878* (2021.01)
*A61M 60/816* (2021.01)

(52) U.S. Cl.
CPC ........ *A61M 60/878* (2021.01); *A61M 60/816* (2021.01); *A61M 2205/3334* (2013.01); *A61M 2205/8262* (2013.01)

(58) Field of Classification Search
CPC .............. A61M 60/878; A61M 60/816; A61M 2205/3334
See application file for complete search history.

(56) References Cited

U.S. PATENT DOCUMENTS 2,254,698 A 9/1941 Hansen, Jr.
2,310,923 A 2/1943 Bean
(Continued)

FOREIGN PATENT DOCUMENTS

AU 7993698 2/1999
AU 2002308409 12/2005
(Continued)

OTHER PUBLICATIONS

International Search Report and Written Opinion received in PCT Application No. PCT/EP2019/064156, dated Aug. 26, 2019 in 10 pages.
(Continued)

*Primary Examiner* — Carl H Layno
*Assistant Examiner* — Maria Catherine Anthony
(74) *Attorney, Agent, or Firm* — Knobbe, Martens, Olson & Bear, LLP

(57) ABSTRACT

The invention relates to a motor housing module (110) for sealing a motor compartment of a motor of a heart support system. The motor housing module (110) has at least one feed-through portion (205), at least one feed-through line (210), and at least one contact pin (215). The feed-through portion (205) is designed to establish an electrical connection between the heart support system and a connection cable in order to externally contact the heart support system. The at least one feed-through line (210) is embedded in the feed-through portion (205) and extends through the feed-through portion (205). The feed-through line (210) can be connected to the motor and to the connection cable. A first
(Continued)

end of the at least one contact pin (215) is embedded in the feed-through portion (205) and a second end of the contact pin (215) projects from the feed-through portion (205) on a side facing away from the motor compartment. The second end of the contact pin (215) can be connected to a sensor line to at least one sensor of the heart support system and to the connection cable.

22 Claims, 5 Drawing Sheets

(56) References Cited

U.S. PATENT DOCUMENTS

| | | |
|---|---|---|
| 3,085,407 A | 4/1963 | Tomlinson |
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,245,622 A | 1/1981 | Hutchins, IV |
| 4,471,252 A | 9/1984 | West |
| 4,522,194 A | 6/1985 | Normann |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,695,471 A | 12/1997 | Wampler |
| 5,702,430 A | 12/1997 | Larson, Jr. et al. |
| 5,713,954 A | 2/1998 | Rosenberg et al. |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A | 6/1999 | Siess et al. |
| 5,921,913 A | 7/1999 | Siess |
| 5,964,694 A | 10/1999 | Siess et al. |
| 6,001,056 A | 12/1999 | Jassawalla et al. |
| 6,007,478 A | 12/1999 | Siess et al. |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,185,460 B1 | 2/2001 | Thompson |
| 6,186,665 B1 | 2/2001 | Maher et al. |
| 6,190,324 B1 | 2/2001 | Kieval et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,324,430 B1 | 11/2001 | Zarinetchi et al. |
| 6,324,431 B1 | 11/2001 | Zarinetchi et al. |
| 6,351,048 B1 | 2/2002 | Schob et al. |
| 6,361,292 B1 | 3/2002 | Chang et al. |
| 6,366,817 B1 | 4/2002 | Kung |
| 6,432,136 B1 | 8/2002 | Weiss et al. |
| 6,445,956 B1 | 9/2002 | Laird et al. |
| 6,447,266 B2 | 9/2002 | Antaki et al. |
| 6,496,733 B2 | 12/2002 | Zarinetchi et al. |
| 6,512,949 B1 | 1/2003 | Combs et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,540,659 B1 | 4/2003 | Milbocker |
| 6,544,216 B1 | 4/2003 | Sammler et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,602,182 B1 | 8/2003 | Milbocker |
| 6,607,368 B1 | 8/2003 | Ross et al. |
| 6,623,475 B1 | 9/2003 | Siess |
| 6,719,791 B1 | 4/2004 | Nüsser et al. |
| 6,731,976 B2 | 5/2004 | Penn et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 7,011,620 B1 | 3/2006 | Siess |
| 7,014,620 B2 | 3/2006 | Kim |
| 7,022,100 B1 | 4/2006 | Aboul-Hosn et al. |
| 7,027,875 B2 | 4/2006 | Siess et al. |
| 7,062,331 B2 | 6/2006 | Zarinetchi et al. |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,155,291 B2 | 12/2006 | Zarinetchi et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,462,019 B1 | 12/2008 | Allarie et al. |
| 7,479,102 B2 | 1/2009 | Jarvik |
| 7,502,648 B2 | 3/2009 | Okubo et al. |

(56) References Cited

U.S. PATENT DOCUMENTS

| | | |
|---|---|---|
| 7,736,296 B2 | 6/2010 | Siess et al. |
| 7,762,941 B2 | 7/2010 | Jarvik |
| 7,798,952 B2 | 9/2010 | Tansley et al. |
| 7,841,976 B2 | 11/2010 | McBride et al. |
| 7,850,593 B2 | 12/2010 | Vincent et al. |
| 7,850,594 B2 | 12/2010 | Sutton et al. |
| 7,878,967 B1 | 2/2011 | Khanal |
| 7,914,436 B1 | 3/2011 | Kung |
| 7,934,909 B2 | 5/2011 | Nuesser et al. |
| 7,959,551 B2 | 6/2011 | Jarvik |
| 7,963,905 B2 | 6/2011 | Salmonsen et al. |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |
| 8,376,926 B2 | 2/2013 | Benkowsi et al. |
| 8,382,695 B1 | 2/2013 | Patel |
| 8,382,830 B2 | 2/2013 | Maher et al. |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,489,200 B2 | 7/2013 | Zarinetchi et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,608,635 B2 | 12/2013 | Yomtov et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,794,989 B2 | 8/2014 | Kearsley et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,308,305 B2 | 4/2016 | Chen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,452,249 B2 | 9/2016 | Kearsley et al. |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,314 B2 | 2/2017 | Aboul-Hosn et al. |
| 9,566,374 B2 | 2/2017 | Spence et al. |
| 9,579,433 B2 | 2/2017 | LaRose et al. |
| 9,585,991 B2 | 3/2017 | Spence |
| 9,592,397 B2 | 3/2017 | Hansen et al. |
| 9,603,984 B2 | 3/2017 | Romero et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,656,010 B2 | 5/2017 | Burke |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,717,833 B2 | 8/2017 | McBride et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,086 B2 | 3/2018 | Dowling et al. |
| 9,919,087 B2 | 3/2018 | Pfeffer et al. |
| 9,950,101 B2 | 4/2018 | Smith et al. |
| 9,950,102 B2 | 4/2018 | Spence et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,327,858 B2 | 6/2019 | Dumesnil |
| 10,342,906 B2 | 7/2019 | D'Ambrosio et al. |

(56) References Cited

U.S. PATENT DOCUMENTS

| | | |
|---|---|---|
| 10,350,342 B2 | 7/2019 | Thomas et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,413,651 B2 | 9/2019 | Yomtov et al. |
| 10,420,869 B2 | 9/2019 | Cornen |
| 10,426,563 B2 | 10/2019 | Dumesnil |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,493,191 B2 | 12/2019 | Whisenant et al. |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,549,020 B2 | 2/2020 | Spence et al. |
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,773,002 B2 | 9/2020 | Siess et al. |
| 10,814,053 B2 | 10/2020 | Throckmorton et al. |
| 10,857,273 B2 | 12/2020 | Hodges et al. |
| 10,857,275 B2 | 12/2020 | Granegger |
| 10,864,308 B2 | 12/2020 | Muller et al. |
| D923,797 S | 6/2021 | Parks et al. |
| D923,798 S | 6/2021 | Goulet et al. |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,299 B2 | 3/2022 | Wolman et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,317,988 B2 | 5/2022 | Hansen et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,438 B2 | 6/2022 | Stewart et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,439,806 B2 | 9/2022 | Kimball et al. |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |

(56) References Cited

U.S. PATENT DOCUMENTS

| | | |
|---|---|---|
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,527,322 B2 | 12/2022 | Agnello et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,744,987 B2 | 9/2023 | Siess et al. |
| 11,745,005 B2 | 9/2023 | Delgado, III |
| 11,746,906 B1 | 9/2023 | Balta et al. |
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,550 B2 | 10/2023 | Siess et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,443 B2 | 11/2023 | Hanson et al. |
| 11,813,444 B2 | 11/2023 | Siess et al. |
| 11,819,678 B2 | 11/2023 | Siess et al. |
| 11,824,381 B2 | 11/2023 | Conyers et al. |
| 11,826,127 B2 | 11/2023 | Casas |
| 11,833,278 B2 | 12/2023 | Siess et al. |
| 11,833,342 B2 | 12/2023 | Tanner et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| 11,857,743 B2 | 1/2024 | Fantuzzi et al. |
| 11,857,777 B2 | 1/2024 | Earles et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| 11,890,212 B2 | 2/2024 | Gilmartin et al. |
| 11,896,199 B2 | 2/2024 | Lent et al. |
| 11,896,482 B2 | 2/2024 | Delaloye et al. |
| 11,898,642 B2 | 2/2024 | Stanton et al. |
| 11,904,104 B2 | 2/2024 | Jahangir |
| 11,911,579 B2 | 2/2024 | Tanner et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,938,311 B2 | 3/2024 | Corbett et al. |
| 11,944,805 B2 | 4/2024 | Stotz |
| 11,980,385 B2 | 5/2024 | Haselman |
| 11,986,604 B2 | 5/2024 | Siess |
| 12,005,248 B2 | 6/2024 | Vogt et al. |
| 12,011,583 B2 | 6/2024 | Wang |
| 12,017,058 B2 | 6/2024 | Kerkhoffs et al. |
| 12,023,476 B2 | 7/2024 | Tuval et al. |
| 12,023,477 B2 | 7/2024 | Siess |
| 12,029,891 B2 | 7/2024 | Siess et al. |
| 12,059,559 B2 | 8/2024 | Muller et al. |
| 12,064,120 B2 | 8/2024 | Hajjar et al. |
| 12,064,611 B2 | 8/2024 | D'Ambrosio et al. |
| 12,064,614 B2 | 8/2024 | Agah et al. |
| 12,064,615 B2 | 8/2024 | Stotz et al. |
| 12,064,616 B2 | 8/2024 | Spanier et al. |
| 12,076,544 B2 | 9/2024 | Siess et al. |
| 12,076,549 B2 | 9/2024 | Stotz et al. |
| 12,090,314 B2 | 9/2024 | Tuval et al. |
| 12,092,114 B2 | 9/2024 | Siess |
| 12,097,016 B2 | 9/2024 | Goldvasser |
| 12,102,815 B2 | 10/2024 | Dhaliwal et al. |
| 12,107,474 B2 | 10/2024 | Vollmer |
| 12,121,713 B2 | 10/2024 | Calomeni et al. |
| 12,144,936 B2 | 11/2024 | Tao et al. |
| 12,144,976 B2 | 11/2024 | Baumbach et al. |
| 12,161,854 B2 | 12/2024 | Earles et al. |
| 12,161,855 B2 | 12/2024 | Hastie et al. |
| 12,171,993 B2 | 12/2024 | Higgins et al. |
| 12,194,287 B2 | 1/2025 | Kassel et al. |
| 2001/0009645 A1 | 7/2001 | Noda |
| 2001/0041934 A1 | 11/2001 | Yamazaki et al. |
| 2002/0076322 A1 | 6/2002 | Maeda et al. |
| 2002/0082585 A1 | 6/2002 | Carroll et al. |
| 2002/0147495 A1 | 10/2002 | Petroff |

(56) References Cited

U.S. PATENT DOCUMENTS

| | | |
|---|---|---|
| 2002/0153664 A1 | 10/2002 | Schroeder |
| 2003/0060685 A1 | 3/2003 | Houser |
| 2003/0091450 A1 | 5/2003 | Davis et al. |
| 2003/0100816 A1 | 5/2003 | Siess |
| 2003/0111800 A1 | 6/2003 | Kreutzer |
| 2003/0139643 A1 | 7/2003 | Smith et al. |
| 2003/0191357 A1 | 10/2003 | Frazier |
| 2003/0199727 A1 | 10/2003 | Burke |
| 2004/0044266 A1 | 3/2004 | Siess et al. |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0008509 A1 | 1/2005 | Chang |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2005/0254976 A1 | 11/2005 | Carrier et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0073352 A1 | 3/2007 | Euler et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |
| 2008/0306328 A1 | 12/2008 | Ercolani |
| 2009/0004037 A1 | 1/2009 | Ito |
| 2009/0112312 A1 | 4/2009 | Larose et al. |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0268017 A1 | 10/2010 | Siess |
| 2010/0298625 A1 | 11/2010 | Reichenbach et al. |
| 2011/0152600 A1 | 6/2011 | Scott et al. |
| 2011/0172505 A1 | 7/2011 | Kim |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2012/0029265 A1 | 2/2012 | LaRose |
| 2012/0035645 A1 | 2/2012 | Gross |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0245404 A1 | 9/2012 | Smith |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0053623 A1 | 2/2013 | Evans |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0030122 A1 | 1/2014 | Ozaki |
| 2014/0051908 A1 | 2/2014 | Khanal et al. |
| 2014/0079557 A1 | 3/2014 | LaRose et al. |
| 2014/0107399 A1 | 4/2014 | Spence |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0303426 A1 | 10/2014 | Kerkhoffs et al. |
| 2014/0309733 A1 | 10/2014 | Cotter |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141842 A1 | 5/2015 | Spanier et al. |
| 2015/0171694 A1 | 6/2015 | Dallas |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0365738 A1 | 12/2015 | Purvis et al. |
| 2015/0374892 A1 | 12/2015 | Yanai et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0067395 A1 | 3/2016 | Jimenez et al. |
| 2016/0144089 A1 | 5/2016 | Woo et al. |
| 2016/0144166 A1 | 5/2016 | Decré et al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0254704 A1 | 9/2016 | Hansen et al. |
| 2016/0256620 A1 | 9/2016 | Scheckel et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0043074 A1 | 2/2017 | Siess |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groß-HardtTim et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0232169 A1 | 8/2017 | Muller |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0093070 A1 | 4/2018 | Cottone |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0199635 A1 | 7/2018 | Longinotti-Buitoni et al. |
| 2018/0207336 A1 | 7/2018 | Solem |
| 2018/0219452 A1 | 8/2018 | Boisclair |
| 2018/0221551 A1 | 8/2018 | Tanner et al. |
| 2018/0221553 A1 | 8/2018 | Taskin |

(56) References Cited

U.S. PATENT DOCUMENTS

| | | |
|---|---|---|
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0256797 A1* | 9/2018 | Schenck ............ A61M 60/414 |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311421 A1 | 11/2018 | Tuseth |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0333059 A1 | 11/2018 | Casas |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0211847 A1 | 7/2019 | Walsh et al. |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0282746 A1 | 9/2019 | Judisch |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0261633 A1 | 8/2020 | Spanier |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0346678 A1 | 11/2021 | Baumbach et al. |
| 2021/0346680 A1 | 11/2021 | Vogt et al. |
| 2021/0379352 A1 | 12/2021 | Schlebusch et al. |
| 2021/0379355 A1 | 12/2021 | Schuelke et al. |
| 2021/0384812 A1 | 12/2021 | Vollmer et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0323742 A1 | 10/2022 | Grauwinkel et al. |
| 2023/0001178 A1 | 1/2023 | Corbett et al. |
| 2023/0091199 A1 | 3/2023 | Siess et al. |
| 2023/0191141 A1 | 6/2023 | Wenning et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0074828 A1 | 3/2024 | Wenning |
| 2024/0075277 A1 | 3/2024 | Schellenberg |
| 2024/0102475 A1 | 3/2024 | Schuelke et al. |
| 2024/0198084 A1 | 6/2024 | Stotz |
| 2024/0245902 A1 | 7/2024 | Schlebusch et al. |
| 2024/0269459 A1 | 8/2024 | Schellenberg et al. |
| 2024/0277998 A1 | 8/2024 | Vogt et al. |
| 2024/0285935 A1 | 8/2024 | Popov et al. |
| 2024/0335651 A1 | 10/2024 | Mitze et al. |
| 2024/0399135 A1 | 12/2024 | Stotz et al. |

FOREIGN PATENT DOCUMENTS

| | | |
|---|---|---|
| AU | 2012261669 | 1/2013 |
| AU | 2013203301 | 5/2013 |

(56) References Cited

FOREIGN PATENT DOCUMENTS

| | | |
|---|---|---|
| AU | 2013273663 | 1/2014 |
| BR | PI0904483-3 | 7/2011 |
| CA | 2 026 692 | 4/1992 |
| CA | 2 026 693 | 4/1992 |
| CA | 2 292 432 | 5/1998 |
| CA | 2 664 835 | 2/2008 |
| CA | 2 796 357 | 10/2011 |
| CA | 2 947 984 | 11/2022 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 101128168 | 2/2008 |
| CN | 201150675 | 11/2008 |
| CN | 101677812 A * | 3/2010 ........... A61B 18/148 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 103915980 | 7/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107921187 | 4/2018 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 27 07 951 | 9/1977 |
| DE | 26 24 058 | 12/1977 |
| DE | 3 545 214 | 7/1986 |
| DE | 4105278 A1 * | 8/1992 .......... A61M 60/829 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 200 13 876 | 9/2001 |
| DE | 100 59 714 | 5/2002 |
| DE | 102 26 305 | 10/2003 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 019 206 | 10/2007 |
| DE | 10 2006 036 948 | 2/2008 |
| DE | 10 2008 060 357 | 6/2010 |
| DE | 10 2009 039 658 | 3/2011 |
| DE | 20 2009 018 416 | 8/2011 |
| DE | 10 2010 041 995 | 4/2012 |
| DE | 11 2009 000 185 | 3/2013 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 904 630 | 3/1999 |
| EP | 0 916 359 | 5/1999 |
| EP | 1 013 294 | 6/2000 |
| EP | 1 186 873 | 3/2002 |
| EP | 1 011 803 | 9/2004 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 314 744 | 4/2011 |
| EP | 2 403 109 | 1/2012 |
| EP | 2 187 807 | 6/2012 |
| EP | 2 330 724 | 8/2012 |
| EP | 1 827 573 | 4/2013 |
| EP | 3 326 567 | 10/2014 |
| EP | 1 898 971 | 3/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |

(56) References Cited

FOREIGN PATENT DOCUMENTS

| | | |
|---|---|---|
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 1 931 403 | 1/2017 |
| EP | 3 127 562 | 2/2017 |
| EP | 2 585 129 | 3/2017 |
| EP | 3 187 210 | 7/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 131 599 | 2/2019 |
| EP | 3 456 367 | 3/2019 |
| EP | 3 478 333 | 5/2019 |
| EP | 3 119 451 | 6/2019 |
| EP | 3 536 360 | 9/2019 |
| EP | 3 542 835 | 9/2019 |
| EP | 3 542 836 | 9/2019 |
| EP | 2 505 090 | 12/2019 |
| EP | 3062877 B1 * 12/2019 ......... A61M 1/1001 | |
| EP | 3 668 560 | 6/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 740 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 821 938 | 5/2021 |
| EP | 3 131 615 | 6/2021 |
| EP | 3 338 825 | 6/2021 |
| EP | 3 432 944 | 6/2021 |
| EP | 3 827 876 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 930 785 | 1/2022 |
| EP | 3 955 985 | 2/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 079 758 | 5/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 711 788 | 8/2022 |
| EP | 3 899 994 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 328 311 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 2 961 984 | 9/2023 |
| EP | 3 352 808 | 9/2023 |
| EP | 2 878 061 | 10/2023 |
| EP | 3 554 576 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 808 390 | 11/2023 |
| EP | 4 061 470 | 11/2023 |
| EP | 3 072 210 | 12/2023 |
| EP | 3 449 958 | 12/2023 |
| EP | 3 687 596 | 12/2023 |
| EP | 3 710 076 | 12/2023 |

(56) References Cited

FOREIGN PATENT DOCUMENTS

| | | |
|---|---|---|
| EP | 3 768 340 | 12/2023 |
| EP | 3 787 707 | 12/2023 |
| EP | 3 926 194 | 12/2023 |
| EP | 3 735 733 | 1/2024 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 768 344 | 7/2024 |
| EP | 3 970 765 | 7/2024 |
| EP | 3 854 444 | 9/2024 |
| EP | 3 534 985 | 10/2024 |
| EP | 3 793 674 | 10/2024 |
| EP | 3 893 957 | 10/2024 |
| EP | 3 914 334 | 10/2024 |
| EP | 3 618 885 | 11/2024 |
| EP | 4 034 221 | 11/2024 |
| EP | 4 087 641 | 11/2024 |
| EP | 4 039 289 | 12/2024 |
| FR | 1458525 | 3/1966 |
| FR | 2 768 056 | 3/1999 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515374 | 9/2001 |
| JP | 2001-515375 | 9/2001 |
| JP | 2003-019197 | 1/2003 |
| JP | 2003525438 A * | 8/2003 ......... G01N 35/1016 |
| JP | 2004-019468 | 1/2004 |
| JP | 2004-278375 | 10/2004 |
| JP | 2005-028137 | 2/2005 |
| JP | 2005-507039 | 3/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6063151 B2 * | 1/2017 ............. A61B 18/12 |
| JP | 6267625 | 1/2018 |
| JP | 2018-057878 | 4/2018 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033047 | 6/2000 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/040218 | 3/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/005228 | 1/2018 |
| WO | WO 2018/007120 | 1/2018 |
| WO | WO 2018/036927 | 3/2018 |
| WO | WO 2018/088939 | 3/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/067233 | 4/2019 |
| WO | WO 2019/078723 | 4/2019 |

(56) References Cited

FOREIGN PATENT DOCUMENTS

| | | |
|---|---|---|
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |
| WO | WO 2023/230157 | 11/2023 |
| WO | WO 2024/243154 | 11/2024 |

OTHER PUBLICATIONS

International Preliminary Report on Patentability and Written Opinion received in PCT Application No. PCT/EP2019/064156, dated Dec. 10, 2020 in 7 pages.
"ABMD—Taking a Closer Look at Impella ECP as the Pivotal Trial Gets Underway", Guggenheim, Press Release, Mar. 29, 2022, pp. 4.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.
Escudeiro et al., "Tribological behavior of uncoated and DLC-coated CoCr and Ti-alloys in contact with UHMWPE and PEEK counterbodies;" Tribology International, vol. 89, 2015, pp. 97-104.
Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.
Neale, Michael J., "The Tribology Handbook;" 1999, Butterworth-Heinemann, Second Edition, pp. 582.
Park et al., "A Novel Electrical Potential Sensing Method for in Vitro Stent Fracture Monitoring and Detection", Jan. 1, 2011, vol. 21, No. 4, pp. 213-222.
Sak et al., "Influence of polyetheretherketone coatings on the Ti-13Nb-13Zr titanium alloy's bio-tribological properties and corrosion resistance;" Materials Science and Engineering: C, vol. 63, 2016, pp. 52-61.
"Edwards SAPIEN 3 Kit—Transapical and Transaortic", Edwards Lifesciences, Released Nov. 8, 2016, p. 11. chrome-extension://efaidnbmnnnibpcajpcglclefindmkaj/https://edwardsprod.blob.core.windows.net/media/De/sapien3/doc-0045537b%20-%20certitude.pdf.
Gopinath, Divya, "A System for Impedance Characterization of Coronary Stents", University of Strathclyde Engineering, Thesis, Aug. 2015, pp. 77.
Ai, X. (2013). Radial Bearings. In: Wang, Q.J., Chung, YW. (eds) Encyclopedia of Tribology. Springer, Boston, MA https://doi.org/10.1007/978-0-387-92897-5_334, accessed Oct. 18, 2024, pp. 4.
GGB by Timken Bearings FAQ; "What is a Slide Bearing?;" https://www.ggbearings.com/en/why-choose-ggb/faq/bearings-faq/what-slide-bearing; accessed Oct. 10, 2024, pp. 1.
Google.com, "Spider Bearing—Search Results;" https://www.google.com/search?q=spider+bearing&rlz=X1C1GCEA_enUS1059US1059&oq=spider+beari&gs_lcrp=EgZjaHJvbWUqCQgAEEUYOxiABDIJCAAQRRg7GIAEMgYIARBFGDkyBwgCEAAYgAQyBwgDEAAYgAQyBwgEEAAYgAQyBwgFEAAYgAQyBwgGEAAYgAQyBggHEEUYPKgCALACAA&sourceid=chrome&ie=UTF-8, accessed Oct. 18, 2024, pp. 4.
McMaster-Carr Online Catalog, "Bearings search results;" https://www.mcmaster.com/products/bearings/; accessed Oct. 18, 2024, pp. 5.
McMaster-Carr Online Catalog, "Slide Bearings search results;" https://www.mcmaster.com/products/slide-bearings/; accessed Oct. 18, 2024, pp. 21.
RBCbearings.com, "RBC Bearings Incorporated—Products;" https://www.rbcbearings.com/Products; accessed Oct. 18, 2024, pp. 2.
SKF.com; "Products: Bearings;" https://www.skf.com/us/products/bearings; accessed Oct. 18, 2024, pp. 8.
Wikipedia, "Plain Bearing," https://en.wikipedia.org/wiki/Plain_bearing; accessed Oct. 18, 2024, pp. 10.

* cited by examiner

MOTOR HOUSING MODULE FOR A HEART SUPPORT SYSTEM, AND HEART SUPPORT SYSTEM AND METHOD FOR MOUNTING A HEART SUPPORT SYSTEM

BACKGROUND

Field

The invention relates to a motor housing module for sealing a motor compartment of a motor of a heart support system and to a heart support system and a method for mounting a heart support system.

Description of the Related Art

Heart support systems, such as a left ventricular heart support system, can be implanted into a heart chamber and have integrated electronic components, such as sensors. Electronic components are mostly integrated into the heart support system in the traditional manner, constructed on substrates, e.g., circuit boards or printed circuit boards (PCBs), and integrated into correspondingly sized cavities of the heart support system. These heart support systems can be implanted by means of a sternotomy, for example. In addition, it is possible to implant more compactly constructed heart support systems, for example also left ventricular heart support systems, into a blood vessel in a minimally invasive manner. Due to the installation size requirements, these more compactly constructed heart support systems do not yet have any integrated electronic components with implanted processing electronics.

U.S. Pat. No. 9,474,840 B2 describes the integration of an optical pressure sensor into the tip of a more compactly constructed heart support system for minimally invasive implantation. The optical supply line is elaborately realized by means of a glass fiber in a channel. The entire evaluation electronics are positioned remotely in an extracorporeal control console as a result of the glass fiber.

For fully implanted systems, however, it is also necessary to implant the processing electronics.

SUMMARY

The object of the invention is to provide an improved heart support system. It is in particular an object of the invention to create electrical connection possibilities in a heart support system in a small installation space both for a motor for driving a blood pump supporting the heart function and for sensors.

This object is achieved by a motor housing module having the features specified in claim 1 and by a heart support system according to claim 14 and the method specified in claim 15 for mounting a heart support system.

Advantageous embodiments of the invention are specified in the dependent claims.

In light of this background, the approach presented here presents a motor housing module for sealing a motor compartment of a motor of a heart support system, a heart support system, and a method for mounting a heart support system according to the main claims. Advantageous developments and improvements of the device specified in the independent claim are possible by means of the measures listed in the dependent claims.

This approach presents a motor housing module for a heart support system. The motor housing module can seal the motor compartment of the heart support system in a fluid-tight manner and connect the motor of the heart support system to a connection cable via which the motor can be supplied with power. In addition, by means of the motor housing module, sensor signals can be combined, processed, and forwarded via the connection cable. The motor housing module and the heart support system can advantageously be designed to be so compact that they can be used, for example, for a left ventricular heart support system (LVAD, left ventricular assist device) for minimally invasive implantation as a fully implanted system. The heart support system can in particular be designed such that it can be inserted into a ventricle or the aorta by means of a catheter.

It is thus advantageously possible to integrate electronic components even in a compactly constructed heart support system.

A motor housing module for sealing a motor compartment of a motor of a heart support system is presented. The motor housing module has a feed-through portion, at least one feed-through line, and at least one contact pin. The feed-through portion is designed to establish an electrical connection between the heart support system and a connection cable for externally contacting the heart support system. The at least one feed-through line is embedded in the feed-through portion and extends through the feed-through portion. The feed-through line can be connected to the motor and the connection cable. A first end of the at least one contact pin is embedded in the feed-through portion, and a second end projects from the feed-through portion on a side facing away from the motor compartment. The second end of the contact pin can be connected to a sensor line to at least one sensor of the heart support system and to the connection cable.

The motor housing module can be designed in one or two parts, for example. For example, the motor housing module can have titanium components or glass components. The heart support system can, for example, be a left ventricular heart support system that has a heart pump with a motor. The motor compartment can, for example, be a portion of the heart support system, e.g., also a housing portion. The motor compartment can advantageously be sealed hermetically, i.e., in a fluid-tight manner, by means of the housing presented here. The motor housing module can, for example, consist of a material that allows a weld connection between the motor or the motor compartment and the motor housing module in order to seal the motor compartment. The feed-through portion for establishing an electrical connection between the heart support system and the connection cable can be designed in one part, for example. Alternatively, the feed-through portion can, for example, comprise a milled part and a glass component which are hermetically connected to one another by laser welding or sintering, for example. The feed-through line and the contact pin can, for example, consist of an electrically conductive material, e.g., a metal, such as an iron-nickel-cobalt alloy, with a low heat expansion coefficient or stainless steel. The connection cable for externally contacting the heart support system can, for example, establish an electrical connection to another implanted component, e.g., a power source and/or control unit of the heart support system. The sensor line can, for example, comprise a group of lines and be designed to forward sensor signals of a sensor in the pump head of the heart support system and/or sensor signals of several sensors. The sensor line can, for example, be realized as an applied flexible thin-film substrate.

According to one embodiment, the feed-through portion can have at least one through-opening filled with an electrically insulating material for embedding the at least one feed-through line and at least one blind hole filled with an electrically insulating material for embedding the at least one contact pin. The feed-through portion can thus advantageously be produced of glass, for example, and both the feed-through line and the contact pin can be embedded. This embodiment advantageously allows a particularly cost-saving production.

It is also advantageous according to one embodiment if the at least one feed-through line and, additionally or alternatively, the at least one contact pin are cylindrical or cup-shaped. If the at least one feed-through line and the at least one contact pin are designed to be cylindrical, i.e., as straight pins, the connection cable can be connected, for example, by soldering, gluing, crimping, or welding the connection cable strands directly to the pin or by using a sleeve or a plug. In the case of a cup-shaped or tulip-shaped forming of the at least one feed-through line and, additionally or alternatively, of the at least one contact pin, the connection to the connection cable can occur, for example, by inserting the strands of the connection cable into the cup of the through line or of the contact pin, wherein the fixing can be realized by means of soldering, gluing, crimping, or welding. According to this embodiment, various application forms can advantageously be realized, which is advantageous with respect to the simplest possible design. In addition, an additional mechanical stabilization of the connection can occur by means of a plug as part of the connection, for example.

According to one embodiment, the motor housing module can comprise a body. The body can have a sensor groove for accommodating at least one electronic component, in particular a sensor, and additionally or alternatively a sensor hub. A sensor can thus advantageously be positioned on the body of the motor housing module, which enables a compact design. The electrical contacting of an electronic component accommodated in the sensor groove with the feed-through portion can, for example, take place by means of an electrically conductive substrate, e.g., a flexible thin-film substrate. The sensor groove can also be formed as a depression or as a cavity, for example. The body can be a milled part made of titanium, for example. The body can be formed, for example, in order to enclose the feed-through portion. The feed-through portion, which can, for example, have glass, can then be hermetically joined to the milled part by laser welding, sintering, or injection molding. Integration of the feed-through portion into the body can be advantageous with respect to the design since the body of the motor housing module can be welded particularly easily to another portion of the heart support system, e.g., the motor compartment or the motor.

If the motor housing module according to one embodiment has a sensor groove, the motor housing module can additionally have a sensor cap for covering the at least one electronic component accommodated in the sensor groove. The sensor cap can, for example, have a metal and be fixed by gluing. This advantageously allows an accommodated electronic component to be protected by the sensor cap.

In addition, according to this embodiment, the motor housing can have a sensor line portion of the sensor line. In the region of the sensor groove, the sensor line portion can form a sensor carrier for connecting the at least one electronic component. The sensor line portion represents a part of the sensor line of the heart support system; the sensor line can be designed modularly for this purpose, for example. For forming the sensor carrier, the sensor line can expand in the region of the sensor line portion, for example. Advantageously, according to this embodiment, connection to the sensor line and integration of an electronic component, such as an additional sensor, is possible in a particularly space-saving and simple manner.

According to one embodiment, the electronic component can have a sensor hub. The sensor hub can be designed to process at least one sensor signal of the at least one sensor of the heart support system. Additionally or alternatively, the sensor hub can be designed to provide the sensor signal via the at least one contact pin to the connection cable. For example, the sensor hub can be understood to be a device that connects nodes of several sensors to one another in the shape of a star, for example. The sensor hub may be a computer network. The sensor hub may be referred to as a coupling element of several sensors. The sensor hub can, for example, connect the sensor at the pump head to a sensor accommodated in the sensor groove of the motor housing module. The connection of several sensors by means of a sensor hub can be advantageous in order to increase reliability with respect to a physical bus network. The sensor hub can, for example, comprise calibration and identification information of the pump and of the sensors of the heart support system and can be read via a communication bus in the connection cable by a central control device of the heart support system. In this way, the control device can be parameterized with motor data, for example. The sensor hub can also be used to pre-process, e.g., to aggregate, to filter, or to calibrate, sensor data of the sensors of the pump and to translate the communication protocol of the sensors into a more robust communication protocol and add artificial redundancy or checksums.

According to one embodiment, the sensor line portion can advantageously have a contact portion. The contact portion can be arranged on a side of the feed-through portion facing away from the motor compartment. In addition, the contact portion can be O-shaped or U-shaped. The contact portion can advantageously be used for electrically contacting the sensor line with the feed-through portion, wherein this embodiment is particularly space-saving. For this purpose, the contact portion can be formed, for example, as an end portion of the sensor line portion and can be folded on or onto the feed-through portion, wherein, as a result of the O-shape or U-shape, the contacting of the connection cable with the at least one contact pin can, for example, be realized without contact of the contact portion to the feed-through line.

According to one embodiment, the contact portion can have at least one contact surface for connection to the at least one contact pin. The contact surface can be formed in order to at least partially enclose the at least one contact pin. For this purpose, the contact surface can be semicircular or elliptical, for example. The contact surface can, for example, have an exposed electrically contactable area, wherein the electrical contact between the sensor line portion and the contact pin can be established by solder or adhesive, for example.

According to one embodiment, the motor housing module can have a connection point cap for covering a connection point between the feed-through portion and the connection cable. This is advantageous in order to protect the connection point. The connection point cap can also be a part of the sensor cap, for example. The connection point cap, like the sensor cap, can be filled with a casting compound, e.g., a silicone or epoxy resin, in order to protect sensors and contact points from corrosion and conductive liquids. The connection point cap can be flexibly formed in order to be able to realize bend protection and strain relief in addition to mechanical protection.

In addition, according to one embodiment, the motor housing module can have a coupling device for coupling an insertion device for inserting the heart support system to the motor housing module, wherein the coupling device can in particular have at least one fixing element. This is advantageous in order to be able to, for example, fix the motor housing module in a form-fitting and/or force-fitted manner to the insertion device in order to, for example, be able to introduce the heart support system, which comprises the motor housing module, in a minimally invasive manner and to decouple it after successful implantation of the insertion device in order to release the heart support system at the destination. The fixing element can, for example, have a clamp or the like. According to one embodiment, the coupling device can be realized on the body of the motor housing module.

A heart support system is also presented. The heart support system has a housing with a motor compartment, a motor arranged in the motor compartment, at least one sensor, a sensor line electrically connected to the at least one sensor, a connection cable for externally contacting the heart support system, and an embodiment of the aforementioned motor housing module as part of the housing. The motor and the at least one sensor are electrically connected to the connection cable by means of the motor housing module.

The heart support system can be a ventricular heart support system, in particular a left ventricular heart support system. The heart support system can, for example, have an electric motor or an electrically operated motor-clutch-pump unit. The sensor can be arranged, for example, on the pump head and, additionally or alternatively, on the motor housing module. The sensor can, for example, be a pressure sensor or a sensor for measuring the blood flow direction. The heart support system can, for example, be cylindrical for minimally invasive insertion and have a diameter that is smaller than that of the human aorta, e.g., 5 to 12 millimeters.

In addition, a method for mounting a heart support system is presented. The heart support system has a motor, a motor compartment, at least one sensor, a sensor line electrically connected to the at least one sensor, and a connection cable for externally contacting the heart support system. The method comprises a step of providing, a step of establishing, a step of contacting, and a step of producing. In the step of providing, an embodiment of the aforementioned motor housing module is provided. In the step of establishing, an electrically conductive connection is established between the at least one feed-through line of the motor housing module and the motor of the heart support system. In the step of producing, a firmly bonded connection is produced between the motor housing module and the heart support system in order to seal the motor compartment of the heart support system. In the step of contacting, the at least one contact pin of the motor housing module is contacted with the sensor line of the heart support system.

The firmly bonded connection can be produced by welding, for example. Optionally, after welding, a sensor cap and, additionally or alternatively, a connection point cap for covering and protecting an electronic component or an electrically conductive interface of a component of the heart support system can also be mounted.

According to one embodiment, the method can also comprise a step of connecting the connection cable of the heart support system to the at least one feed-through line and the at least one contact pin of the motor housing module. The step of connecting can take place before or after the step of producing. If the step of connecting is after the step of producing, the motor housing module can have a passage opening for the connection cable.

This method can, for example, be implemented in software or hardware or in a mixed form of software and hardware in a control device, for example.

A computer program product or computer program having program code which can be stored in a machine-readable carrier or storage medium, such as a semiconductor memory, a hard drive memory, or an optical memory, and is used to carry out, implement, and/or control the steps of the method according to one of the embodiments described above is also advantageous, in particular if the program product or program is executed on a computer or a device.

BRIEF DESCRIPTION OF THE DRAWINGS

Advantageous exemplary embodiments of the approach presented here are shown in the drawings and explained in more detail in the following description. The drawings show.

DETAILED DESCRIPTION

In the following description of favorable exemplary embodiments of the present invention, the same or similar reference signs are used for the elements which are shown in the various figures and have a similar effect, wherein a repeated description of these elements is omitted.

Figure 1:
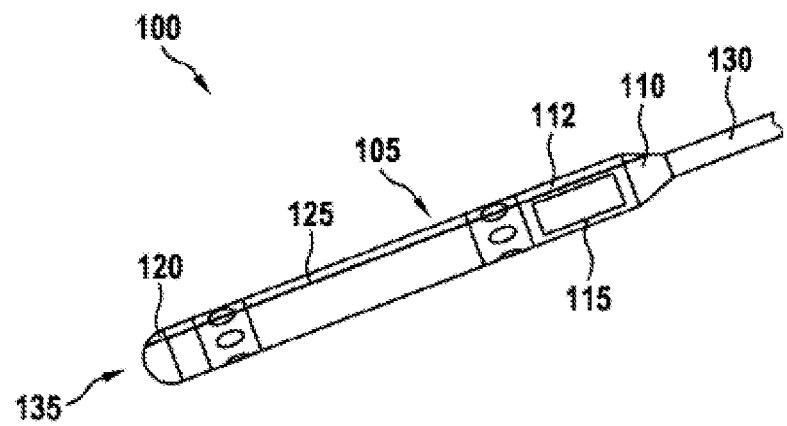
FIG. 1 a schematic illustration of a heart support system according to an exemplary embodiment.

FIG. 1 shows a schematic illustration of a heart support system 100 according to an exemplary embodiment. Shown is a side view of the heart support system 100, which is designed here, by way of example, as a left ventricular heart support system 100. The heart support system 100 has a housing 105. As part of the housing 105, the heart support system 100 comprises a motor housing module 110. A motor compartment 112 is enclosed by the housing 105 and the motor housing module 110. A motor 115 is arranged in the motor compartment 112. At least one sensor 120 is arranged in a sensor assembly on a head side of the heart support system 100. The sensor 120 is electrically connected to a sensor line 125. The sensor line 125 is laid here, by way of example, across the housing 105 to the motor housing module 110; it can also run at least in portions within the housing 105 or be laid in the shape of a spiral across the housing 105. The sensor 120 can, for example, be a pressure sensor or a flow sensor for blood flow measurement by means of ultrasound or laser, for example. On the side of the motor housing module 110 facing away from the motor compartment 112, the heart support system 100 has a connection cable 130 for externally contacting the heart support system 100. The motor housing module 110 can be referred to as an electrical connecting element: The motor 115 and the at least one sensor 120 are electrically connected to the connection cable 130 by means of the motor housing module 110. The motor housing module 110, also called the motor backend, is formed to hermetically seal the motor compartment 112 and thus to seal it in a fluid-tight manner. In addition, the motor housing module 110 is designed to establish an electrical connection between the hermetically sealed motor interior of the motor 115 and the surroundings of the heart support system 100: The motor housing module 110 assumes the tasks of joining the sensor line 125, which conducts electrical signals from a pump head 135 of the heart support system 100 to the motor housing module 110, to the connection cable 130, which forwards the sensor signals and supplies the motor with electrical energy. For this purpose, electrical conductors from the interior of the motor 115 can be joined to the sensor cable 125 laid on the outside of the motor 115 and to the connection cable 130, also called supply cable. In this way, a mechanically secure connection of the connection cable 130 to the motor housing module 110 can be established. Via the connection cable 130, the heart support system 100 can be connected to another component, such as an energy source, a data processing device, or a control device.

The heart support system 100 has a cylindrical, elongated structure with a substantially constant outer diameter and rounded, tapered ends for easy positioning by means of a catheter in a blood vessel, e.g., the aorta. The motor housing module 110 has the shape of a truncated cone. It is conically formed, with a base surface in the direction of the motor compartment 112, which corresponds to the outer diameter of the heart support system 100, and with a smaller top surface as a transition to the connection cable 130.

Figure 2:
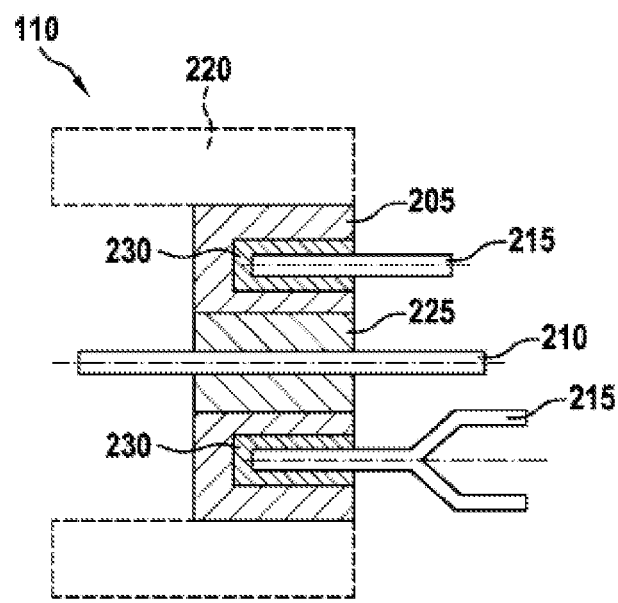
FIG. 2 a schematic illustration of a motor housing module according to an exemplary embodiment.

FIG. 2 shows a schematic illustration of a motor housing module 110 for sealing a motor compartment of a motor of a heart support system according to an exemplary embodiment. The motor housing module 110 corresponds or is similar to the motor housing module 110 of FIG. 1. A cross-section of a side view of the motor housing module 110 is shown. The motor housing module 110 has at least one feed-through portion 205 for establishing an electrical connection between the heart support system and a connection cable for externally contacting the heart support system. In addition, the motor housing module 110 has at least one feed-through line 210, which is embedded in the feed-through portion 205 and extends through the feed-through portion 205. The feed-through line 210 can be connected to the motor and the connection cable of the heart support system. The motor housing module 110 furthermore has at least one contact pin 215. For example, two differently formed contact pins 215 are shown here. A first end of the contact pin 215 is embedded in the feed-through portion 205 and a second end projects from the feed-through portion 205 on a side facing away from the motor compartment. The second end of the contact pin 215 can be connected to a sensor line to at least one sensor of the heart support system and to the connection cable.

As in the exemplary embodiment shown here, the feed-through portion 205 can have at least one through-opening 225 filled with an electrically insulating material for embedding the at least one feed-through line 210 and at least one blind hole 230 filled with an electrically insulating material for embedding the at least one contact pin 215. One of the blind holes can also be filled conductively, e.g., with an electrically conductive adhesive, in order to establish an electrical connection between the motor housing and a conductor of the connection cable. This can serve to electrically shield the motor and connection cable, for example. The feed-through portion 205 is formed from titanium, for example. The through-opening 225 and the two blind holes 230 shown are formed in the feed-through portion 205 and filled, for example, with glass as electrically insulating material. The blind holes 230 can accordingly also be referred to as blind glass feed-throughs since they do not lead all the way into the interior of the hermetically sealed motor. The feed-through line 210, which can be realized as a feed-through pin or pin, is used to electrically contact the motor. The contact pins 215, also called blind pins, are used to rewire the sensor line. The feed-through line 210 as well as the at least one contact pin 215 are formed from an electrically conductive material, e.g., from a metal, such as an iron-nickel-cobalt alloy, with a low thermal expansion coefficient or such as stainless steel.

The at least one feed-through line 210 and/or the at least one contact pin 215 can be designed to be cylindrical, i.e., as straight pins, as shown here by way of example in the case of the feed-through line 210 and the upper of the two contact pins 215. The feed-through line 210 and/or the at least one contact pin 215 can alternatively also be cup-shaped, as shown by way of example in the case of the lower of the two contact pins 215. If the feed-through line 210 and/or the at least one contact pin 215 are cylindrical, the connection cable can be connected, for example, by soldering, gluing, crimping, or welding the connection cable strands directly to the feed-through line 210 and/or the contact pin 215 or by using a sleeve or a plug. If the feed-through line 210 and/or the at least one contact pin 215 are cup-shaped, the cable connection to the connection cable can be realized by inserting the strands into the cup. Fixing can take place by soldering, gluing, crimping, or welding.

Figure 6:
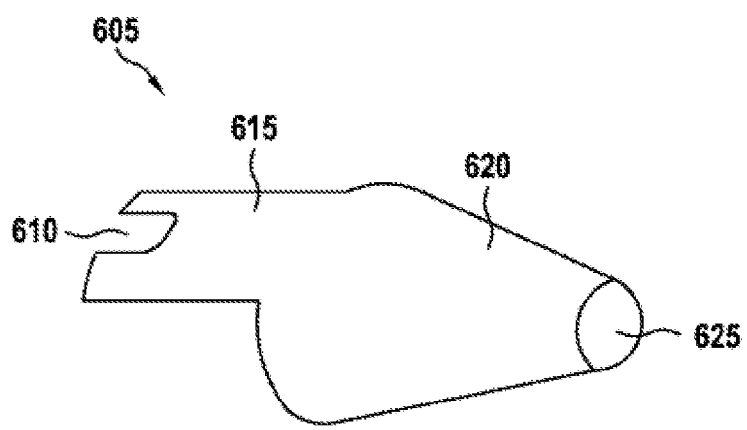
FIG. 6 a schematic illustration of a cap element for a motor housing module according to an exemplary embodiment.

According to the exemplary embodiment shown in FIG. 2, the motor housing module 110 is designed in two parts, with a body 220 and the feed-through portion 205, which is formed, for example, as a so-called glass feed-through component. The two-part design of the motor housing module 110 is advantageous in terms of production technology. In this case, the electrical contacting of the motor and the sensor line with the feed-through portion 205 can be made possible in the interior of the motor housing module 110, hereinafter also referred to as backend, wherein motor strands can be soldered to the feed-through portion 205, for example. An advantage of the two-part design of the motor housing module 110 is that a standard glass feed-through can be used for the feed-through portion 205, which can then, for example, be hermetically joined to the body 220 designed as a milled part by laser welding, sintering, or insert molding, wherein the body can have additional features, such as the integration of clamps as fixing element of the coupling device and a sensor depression in the form of the sensor groove, as described, for example, with reference to FIG. 8. The two-part design of the motor housing module 110 is also advantageous with respect to the assembly since the following production procedure can be implemented, for example: contacting the feed-through portion 205 with the motor interior; connecting the feed-through portion 205 to the body 220 by sliding the body 220 onto and over the feed-through portion 205, for example; welding the body 220 to the motor housing 112; welding the body 220 to the feed-through portion 205; establishing an electrical connection of the sensor cable to the contact pins 215; and contacting the connection cable with the feed-through line 210 and the contact pins 215. The mounting of a cap element as a protective cap as shown in FIG. 6 can then optionally take place by casting.

The two-part design of the motor housing module 110 can be realized by a combination of a milled part as a body 220 for producing the corresponding geometry with advantageous mechanical robustness and strength and by a feed-through portion 205 with classic glass feed-throughs. The body 220 as a milled part can advantageously be formed from titanium in order to be able to weld the motor housing module 110 particularly easily and efficiently to a motor housing 112 of the motor 115, which can also consist of titanium, for example. In this way, a hermetically sealed connection can be established between the body 220 and the motor housing 112 in order to seal the motor compartment in a fluid-tight manner. The forming of the contact pins 215 as glass blind pins, i.e., as blindly ending glass feed-through, allows robust rewiring of the flexible sensor line to the connection cable on the basis of glass feed-through technology by means of the possibility of connecting the contact pins 215 to the sensor line and to the connection cable. FIG. 2 thus shows a backend or motor housing module 110 with blind pins for rewiring in the form of the two contact pins 215 shown, by way of example, in the blind holes 230.

Figure 3:
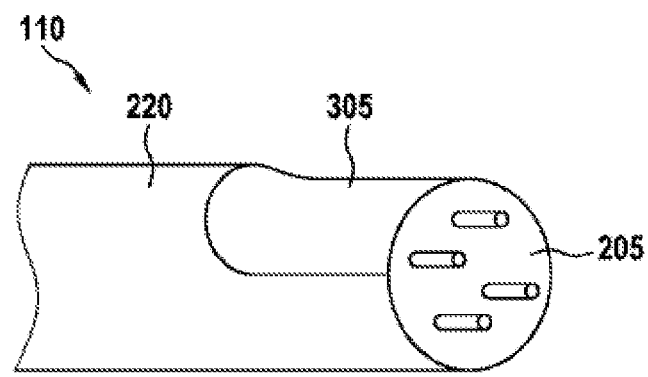
FIG. 3 a schematic illustration of a motor housing module according to an exemplary embodiment.

FIG. 3 shows a schematic illustration of a motor housing module 110 according to an exemplary embodiment. A side view of the motor housing module 110 with the body 220 and the feed-through portion 205 is shown, wherein the feed-through portion 205 for embedding the feed-through line and the at least one contact pin is formed and has, by way of example, recesses for this purpose.

The motor housing module 110, also called the pump backend, has a cylindrical shape with a depressed plane in the direction of the feed-through portion 205. For example, a sensor can be positioned on this depressed plane. The depressed plane can be formed as a depression or as a cavity or as a groove. According to the exemplary embodiment shown here, the body 220 correspondingly has a sensor groove 305 in the form of the depressed plane for accommodating at least one electronic component, in particular a sensor and/or a sensor hub.

An electrically conductive substrate can be arranged in the sensor groove 305 in order to realize an electrical contact of an electronic component accommodated in the sensor groove 305. The substrate can be formed, for example, in order to connect the electrical component accommodated in the sensor groove 305 to electrically conductive pins of the backend, i.e., to the at least one contact pin embedded in the feed-through portion 205. The substrate is a flexible thin-film substrate, for example. According to the exemplary embodiment shown in the following FIG. 4, the substrate can also be part of the sensor line or of a sensor line portion.

Figure 8:
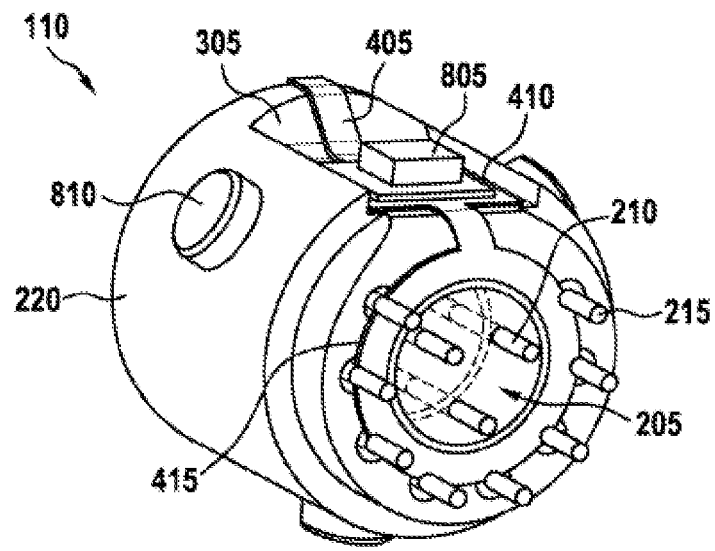
FIG. 8 a schematic illustration of a motor housing module according to an exemplary embodiment.

The motor housing module 110 can optionally have a coupling device for coupling an insertion device with the heart support system, as shown in FIG. 8. In addition, the motor housing module 110 can optionally have a fit for attaching a cap element as shown in FIG. 6 as a protective cap or as a bend protection grommet. The cap element can be formed, for example, in order to cover the sensor groove 305 and the feed-through portion 205.

The body 220 can be formed from the same material as the motor of the heart support system in order to be able to establish a hermetic welded connection between the motor and the backend in the form of the motor housing module 110. A fixed connection, e.g., by ultrasonic welding or injection molding of a polymer, is also possible, as well as sintering processes and glazing processes of ceramic components, for example. The feed-through portion 205, which can realize both an electrical feed-through into the hermetically sealed interior and a rewiring for the sensor line, is significant for the use of the motor housing module 110 as an electrical connecting element. Manufacturing the motor housing module 110 of one part dispenses with a weld seam and requires correspondingly formed glass feed-throughs for the feed-through portion 205.

Figure 4:
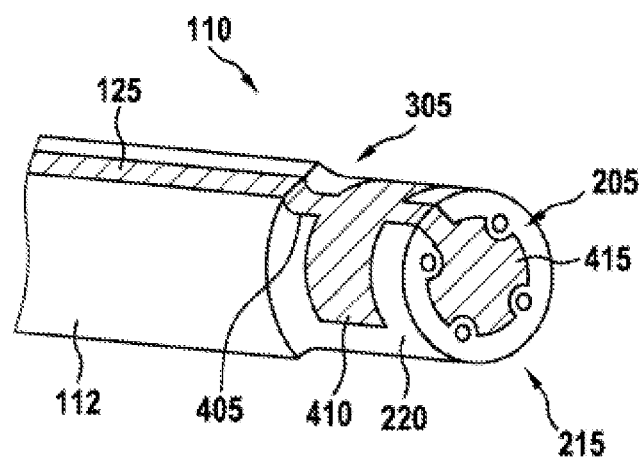
FIG. 4 a schematic illustration of a motor housing module according to an exemplary embodiment.

FIG. 4 shows a schematic illustration of a motor housing module 110 according to an exemplary embodiment. A side view of the motor housing module 110 connected to the motor compartment 112 of the heart support system is shown, wherein only a proximal portion of the cylindrical heart support system comprising the motor compartment 112 is shown of the heart support system. On the side facing the motor compartment 112, the motor housing module 110 has the same diameter and the same material as the motor compartment 112. In order to form a sensor groove, the motor housing module 110 can taper conically in order to create installation space for positioning sensors. The sensor line 125 is laid here, by way of example, along the longitudinal axis of the heart support system 100 in a band-shaped manner on the housing of the heart support system across the motor chamber 112 to the motor housing module 110.

According to the exemplary embodiment shown here, the motor housing module 110 comprises a sensor line portion 405 of the sensor line 125. In the region of the sensor groove 305, the sensor line portion 405 has a sensor carrier 410 for connecting the at least one electronic component. The sensor carrier 410 can also be understood as a portion, e.g., a planar region, of the motor housing module 110. The sensor line portion 405 is formed, for example, for integrating a sensor in the sensor groove 305.

The sensor line 125 and the sensor line portion 405 can be formed from an electrically conductive flexible thin-film substrate. The sensor groove 305 is formed here in a band-shaped manner circumferentially around the motor housing module 110. The sensor line portion 405 is connected to the sensor line 125 and extends in one part along the sensor groove 305 around a portion of the lateral surface of the motor housing module 110, wherein the sensor line portion 405 is expanded in this region in order to allow several sensor carriers 410 for connecting several electronic components to be formed on the sensor line portion 405 along the sensor groove 305, as shown in the following FIG. 5. The shaping of the sensor groove 305 can be designed according to the exemplary embodiment shown here in order to enable both the cable routing of the sensor line 125 in the described portion of the sensor line portion 405 and the sensor integration on the sensor line portion 405 in the sensor groove 305. In another part, the sensor line portion 405 extends in the direction of the feed-through portion 205 from the sensor groove 305 toward the cross-sectional area of the feed-through portion 205.

According to the exemplary embodiment shown here, the sensor line portion 405 has a contact portion 415. The contact portion 415 is arranged on a side of the feed-through portion 205 facing away from the motor compartment 112. The contact portion 415 is arranged at least partially on the feed-through portion 205. The contact portion 415 can be O-shaped or U-shaped. Here, the contact portion 415 extends, by way of example, over a large part of the cross-sectional area of the feed-through portion 205.

According to the exemplary embodiment shown here, the contact portion 415 has recesses in the region of the through-opening and/or of the blind holes. In order to contact the at least one contact pin 215 with the sensor line 125, the sensor line portion 405 can have an exposed, electrically contactable region in the form of an electrically conductive contact surface 510, which connects to the at least one contact pin 215 embedded in the feed-through region 205. By way of example, four contact pins 215 are shown here. The contact portion 415 has, per contact pin 215, a semicircular recess 510 adjacent to the contact pins. The sensor line portion 405, and thus the sensor line 125, is electrically connected via the contact portion 415 to the contact pins 215 in the feed-through portion 205 of the motor module housing 110. This design of the connection can also be referred to as a connection of the flexible sensor line 125, also called sensor flex, to the blind pins in the form of the contact pins 215.

Figure 5:
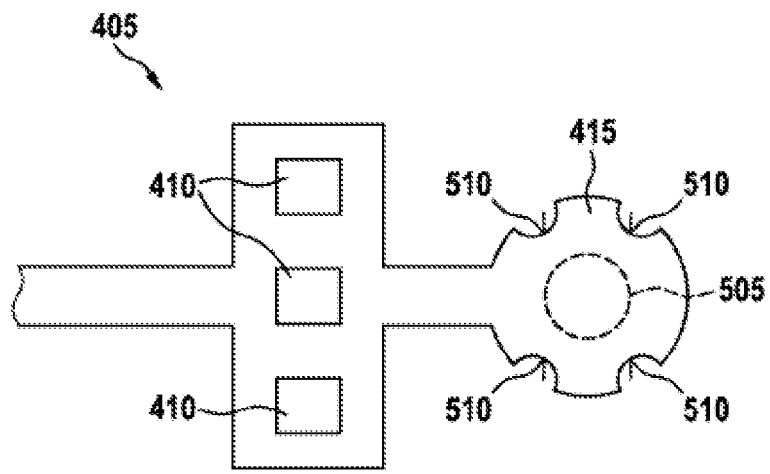
FIG. 5 a schematic illustration of a sensor line portion of a motor housing module according to an exemplary embodiment.

FIG. 5 shows a schematic illustration of a sensor line portion 405 of a motor housing module according to an exemplary embodiment. Here, the sensor line portion 405 is designed, by way of example, as a thin-film substrate for contacting the blind pins in the form of contact pins and for integrating additional sensors of the heart support system on the motor housing module and is shown in a top view as a fold. The form of the sensor line portion 405 shown here is suitable for contacting the sensor line to the motor housing module and enables sensor integration on the sensor line portion 405. The form of the sensor line portion 405 substantially corresponds to that of the sensor line portion 405 described in FIG. 4, with the expansion of the sensor line portion 405 into a circumferential portion, which corresponds to the sensor groove, around the motor housing module. In this region of the expansion of the sensor line portion 405, three sensor carriers 410 are formed, by way of example, in the exemplary embodiment shown here. Electronic components, for example sensors, can be integrated on these sensor carriers 410. Here, the contact portion 415 additionally has an O-shaped recess 505, through which the feed-through line can be fed through if the contact portion 415 lies on the feed-through portion 205.

The contact portion 415 comprises at least one contact surface 510 for connecting to the at least one contact pin. The at least one contact surface 510 is formed in order to at least partially enclose the at least one contact pin. The contact surface 510 can also be referred to as a contact pad. According to the exemplary embodiment shown here, the contact portion 415 has, by way of example, four contact surfaces 510 in order to electrically connect four contact pins embedded in the feed-through portion to the sensor line portion 405. Depending on the form of the contact portion 415, the contact surfaces 510 can be semicircular or elliptical in order to at least partially enclose one contact pin each for electrically contacting with the sensor line portion 405. The forms of the motor housing module and of the sensor line are, for example, adapted to each other by the forming of the sensor line portion 405 such that the contact pads 510 enclose the contact pins of the motor housing module. For this purpose, the contact pads 510 have an exposed, electrically contactable region. An electrical contact can be established by solder or adhesive, for example. The contacting of the feed-through line to connect the motor can take place in the same way as the contacting of the contact pins with the sensors, or the contact portion 415 has, as shown here, the recess 505 in the shape of an O or U so that a connection of the feed-through line to the connection cable without contact to the contact portion 415 of the sensor line portion 405 is possible. The arrangement of the contact portion 415 on the feed-through portion, and thus the contacting of the sensor line to the blind pins of the motor housing module, can take place in the production process, e.g., by folding the sensor line portion 405 onto the feed-through portion and subsequently producing the electrical connections.

Additional installation space for accommodating electronic components, such as sensors, in the sensor groove can be created by additional depressions in the sensor groove of the motor housing module, in particular if the sensor line section 405 has several sensor carriers 410 as shown here. Components accommodated in the sensor groove can additionally be mechanically protected by a cap element.

According to one exemplary embodiment, an electronic component accommodated on the sensor line portion 405 in the sensor groove of the motor housing module can have a sensor hub. The sensor hub is designed to process at least one sensor signal of the at least one sensor of the heart support system. Additionally or alternatively, the sensor hub is designed to provide at least one sensor signal via the at least one contact pin to the connection cable. The integration of a sensor hub enables the pre-processing of sensor data and the translation of the data interfaces. In addition, calibration parameters and operating parameters, such as identification information of the heart support system or accommodated sensors, can be stored in the heart support system by means of the sensor hub and can be provided by means of the connection cable to a connected control device, e.g., via a communication bus in the connection cable. In this way, the control device can be parameterized with motor data, for example. The sensor hub can be used to pre-process, e.g., to aggregate, to filter, or to calibrate, sensor data from sensors of the heart support system pump and to translate the communication protocol of the sensors into a more robust communication protocol (transceiver) and add artificial redundancy or checksums.

FIG. 6 shows a schematic illustration of a cap element 605 for a motor housing module according to an exemplary embodiment. The cap element 605 is provided for use with the motor housing module of one of the figures shown here. The cap element 605 is formed to cover electronic components of a motor housing module, as described with reference to FIG. 3. The cap element 605 can therefore be used as mechanical protection of the motor housing module. A side view of the cap element 605 is shown in a one-piece design.

In the direction of the motor compartment, the cap element 605 has at least one recess 610 as a sensitive measurement window for one of the sensors 120/410/710. The sensor can, for example, be a pressure sensor so that the measurement window 610 is to be positioned above the pressure-sensitive membrane of the pressure sensor so that the blood pressure of the surrounding blood can act in an unimpeded manner on the pressure sensor. Adjacent to the recess 610, the cap element has the sensor cap 615. The sensor cap is formed in order to create a sensor groove, e.g., the sensor groove described in FIG. 3, which is formed by way of example as a depressed plane of the cylindrical body of the motor housing module. If the sensor groove is formed, for example, according to the exemplary embodiments described in FIGS. 4 and 5 as a circumferential depression, the sensor cap can be formed correspondingly to cover this region. Formed conically in the manner of an arrow tip, a connection point cap 620, which has an opening 625 for feeding through the connection cable, adjoins the sensor cap 615.

According to the exemplary embodiment shown here, the cap element 605 thus has the sensor cap 615 for covering the at least one electronic component accommodated in the sensor groove. The cap element 605 furthermore has the optional connection point cap 620 for covering a connection point between the feed-through portion and the connection cable. The sensor cap 615 and the connection point cap 620 can, as shown here, be designed as a combined one-piece component as cap element 605.

Alternatively, the sensor cap 615 and the connection point cap 620 can also be designed as respectively separate components. In this case, the sensor cap 615 can, for example, be a metallic cap that is fixed by gluing. The connection point cap 620 can be formed flexibly, for example, in order to enable bend protection and strain relief in addition to mechanical protection. The cap element 605 can, for example, be filled with a casting compound, e.g., a silicone or epoxy resin, in order to protect sensors and contact points from corrosion and conductive liquids.

Figure 7:
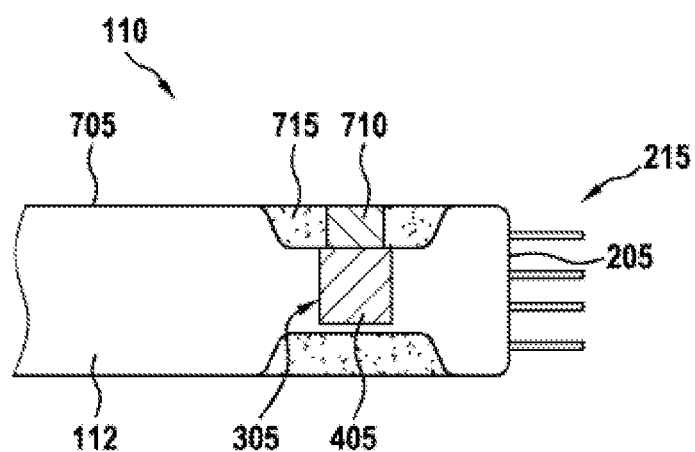
FIG. 7 a schematic illustration of a motor housing module according to an exemplary embodiment.

FIG. 7 shows a schematic illustration of a motor housing module 110 according to an exemplary embodiment. Here, the motor housing module 110 corresponds or resembles the motor housing module of one of the above-described figures. The side view shows, as a section of the mounted cylindrical heart support system, the motor compartment 112 with a motor compartment housing 705. The motor housing module 110 is connected to the motor compartment housing 705 and has, in the direction of the motor compartment 112, a circumferential depression as a sensor groove 305. In the region of the sensor groove 305, a sensor 710 is integrated, by way of example, as an electronic component on the sensor line portion 405. In order to illustrate the possibility of filling the sensor 710 with a casting compound using the sensor cap and/or the cap element, as described with reference to the previous FIG. 6, the correspondingly filled region 715 is shown here by way of example. On the side facing away from the motor compartment 112, the motor housing module 110 has the feed-through portion 205, from which four contact pins 215 project by way of example.

FIG. 8 shows a schematic illustration of a motor housing module 110 according to an exemplary embodiment. The motor housing module 110 is shown here in a top view. The body 220 is realized as a titanium part. For the electrical functionalization of the motor housing module 110 as an electrical connecting element, the sensor line portion 405 is laid from the direction of the motor compartment into the sensor groove 305. The sensor line portion 405 is here formed as a thin-film substrate by way of example. The body 220 in the form of a milled part made of titanium has a depressed plane as a sensor groove 305. The sensor line portion 405 expands in the region of the sensor groove 305 and, as a thin layer, almost completely fills a lower region of the base surface of the sensor groove 305. A sensor carrier 410, on which, by way of example, an electronic component 805 is accommodated, is located in the sensor groove 305 on the sensor line portion 405.

According to one exemplary embodiment, the motor housing module 110 has a coupling device for coupling with the motor housing module 110 an insertion device for inserting the heart support system, wherein the coupling device in particular has at least one fixing element 810. The fixing element 810 can serve for the form-fitting coupling of a clamp element, a so-called clamp. The body 220, as a titanium part, has here, by way of example, three round fixing elements 810 as a coupling device. The fixing elements 810 can additionally or alternatively also be used to fix a cap element for covering an electronic component 805 or an electrical connection point of the motor housing module 110; the fixing elements 810 then serve as a fit for attaching the cap element.

The exemplary embodiment of the motor housing module 110 shown here has the body 220 and the feed-through portion 205 realized as a so-called glass feed-through. By way of example, three feed-through lines 210 for electrically connecting the motor of the heart support system to the connection cable are embedded in the feed-through portion 205. In addition, eight contact pins 215 arranged in the shape of a U are embedded in the feed-through portion 205 by way of example. The contact pins 215 are spaced apart substantially evenly. Tapered in the shape of a band in the direction of the feed-through portion 205, the sensor line portion 405 is guided out of the sensor groove 305 and forms the O-shaped contact portion 415. Adjacent to the contact pins 215, the contact portion 415 respectively has a semicircular contact surface for electrically connecting the contact pins 215 to the sensor line portion 405. The connection cable can be connected to the feed-through line 210 and to the contact pins 215 in order to externally contact the heart support system by means of the motor housing module 110.

Figure 9:
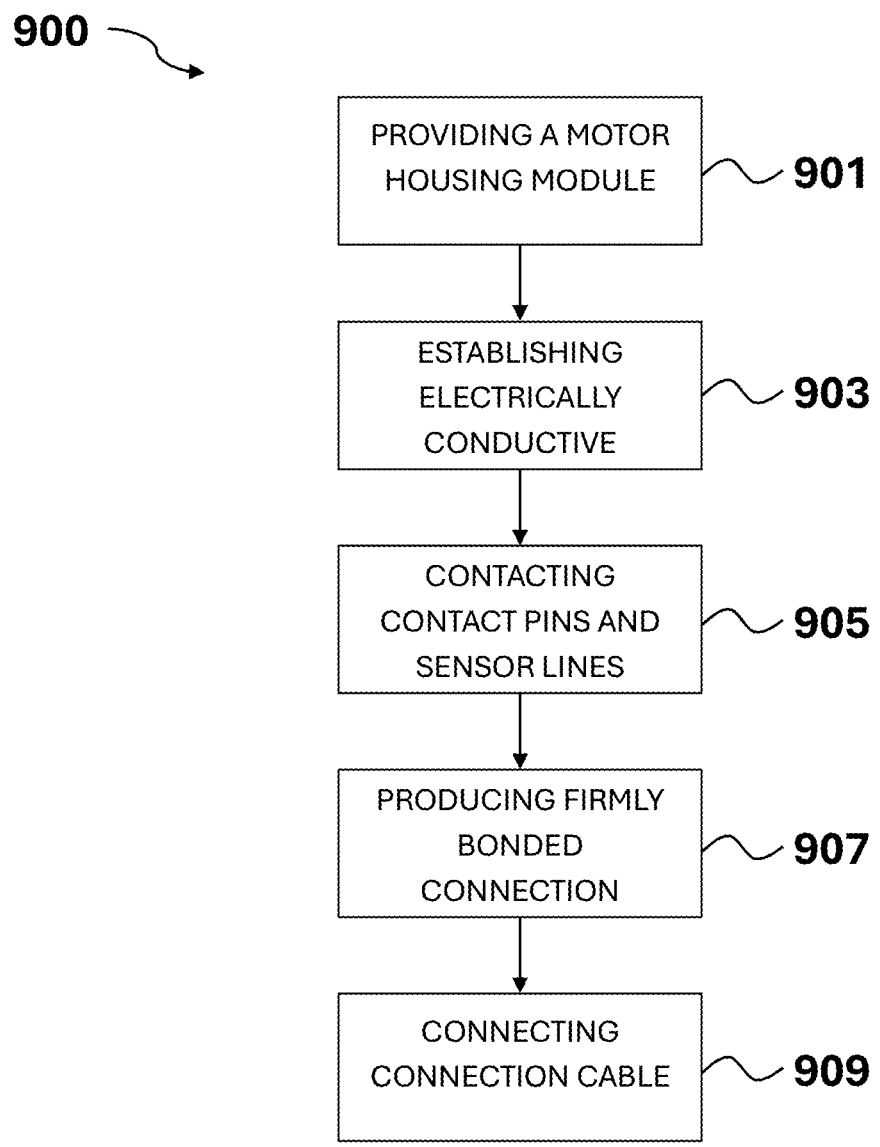
FIG. 9 a flow diagram of a method for mounting a heart support system according to an exemplary embodiment.

FIG. 9 shows a flow diagram of a method 900 for mounting a heart support system according to an exemplary embodiment. The heart support system has a motor, a motor compartment, at least one sensor, a sensor line electrically connected to the at least one sensor, and a connection cable for externally contacting the heart support system. The method 900 comprises a step 901 of providing, a step 903 of establishing, a step 905 of contacting, and a step 907 of producing. In step 901 of providing, a motor housing module is provided. Here, the motor housing module corresponds or resembles the motor housing module of one of the above-described figures. In step 903 of establishing, an electrically conductive connection is established between the at least one feed-through line of the motor housing module and the motor of the heart support system. In step 905 of contacting, the at least one contact pin of the motor housing module is contacted with the sensor line of the heart support system. In step 907 of producing, a firmly bonded connection is produced between the motor housing module and the heart support system in order to seal the motor compartment of the heart support system. In addition, in step 907 of producing, a sensor cap and/or a connection point cap for covering and protecting an electronic component or an electrically conductive interface of a component of the heart support system can optionally be mounted.

A sequence of the steps of the method presented here can also be provided in a special exemplary embodiment as follows:
1. Attaching the feed-through pin to the motor interior
2. Positioning the body 220
3. Tightly welding the body to the motor housing so that the connection established in this way is retained mechanically
4. Tightly welding the contact element in the body
5. Affixing the sensor line 125, folding the contact portion 415 onto the feed-through portion 205, contacting the contact surface 510 to the contact pin 215
6. Contacting the sleeves to wires of the connection cable 130
7. Sliding the contacted sleeves onto contact pin 215 and feed-through line 210 and welding them thereto
8. Casting and positioning the sensor cap 615 and the connection point cap 620

According to one exemplary embodiment, the method 900 optionally has a step 909 of connecting the connection cable of the heart support system to the at least one feed-through line and the at least one contact pin of the motor housing module. The step 909 of connecting can be carried out before or after step 907 of producing.

If an exemplary embodiment includes an "and/or" conjunction between a first feature and a second feature, this should be read to mean that the exemplary embodiment according to one embodiment comprises both the first feature and the second feature and according to another embodiment comprises either only the first feature or only the second feature.

The invention claimed is:

1. A heart support system, comprising:
   a blood pump;
   a motor compartment;
   a motor arranged in the motor compartment and configured to drive the blood pump;
   at least one sensor disposed on a surface of the blood pump;
   a motor housing module comprising:
      a feed-through portion configured to establish an electrical connection between the heart support system and a connection cable; and
      at least one contact terminal, wherein the at least one contact terminal is configured to form a connection between the connection cable and the at least one sensor via an electrical connection external to the motor housing module, wherein the at least one contact terminal has a distal end embedded in a blind hole electrically insulated from the interior of the motor compartment and a proximal end that protrudes proximally beyond the motor housing module, wherein the blind hole is disposed on a side of the motor housing module opposite a pump head of the blood pump, and wherein the at least one contact terminal is accessible from a side of the motor housing module facing away from the motor compartment; and
   at least one feed-through line extending through the motor housing module, wherein the at least one feed-through line is configured to connect to the motor.

2. The heart support system according to claim 1, wherein the at least one contact terminal is configured to connect to a conductor of the connection cable.

3. The heart support system according to claim 1, wherein the at least one contact terminal comprises at least one contact pin.

4. The heart support system according to claim 3, wherein the feed-through portion comprises at least one through-opening filled with an electrically insulating material configured to facilitate embedding the at least one feed-through line and at least one blind hole filled with an electrically insulating material configured to facilitate embedding the at least one contact terminal.

5. The heart support system according to claim 1, wherein the at least one feed-through line and/or the at least one contact terminal is cylindrical or cup-shaped.

6. The heart support system according to claim 1, wherein the motor housing module comprises a sensor groove configured to receive the at least one sensor and/or a sensor hub.

7. The heart support system according to claim 6, wherein the sensor groove is configured to receive the at least one sensor, the heart support system further comprising a sensor cap positioned at least partially over the sensor groove and having a measurement window for the at least one sensor within the sensor groove.

8. The heart support system according to claim 6, further comprising a sensor line portion comprising a sensor carrier in a region of the sensor groove, the sensor carrier being configured to connect to the sensor and/or the sensor hub.

9. The heart support system according to claim 8, wherein the sensor groove is configured to receive the sensor hub, and wherein the sensor hub is configured to process at least one sensor signal of the at least one sensor and/or to provide the at least one sensor signal to the connection cable.

10. The heart support system according to claim 8, wherein the sensor line portion comprises a contact portion, wherein the contact portion is arranged on a side of the feed-through portion facing away from the motor compartment.

11. The heart support system according to claim 10, wherein the contact portion is O-shaped or U-shaped.

12. The heart support system according to claim 10, wherein the contact portion comprises at least one contact surface for connecting to the at least one contact terminal, and wherein the at least one contact surface is formed to at least partially enclose the at least one contact terminal.

13. The heart support system according to claim 1, having a connection point cap configured to cover a connection point between the feed-through portion and the connection cable.

14. The heart support system according to claim 1, further comprising a coupling device for coupling the motor housing module to an insertion device configured to insert the heart support system, wherein the coupling device comprises at least one fixing element.

15. The heart support system according to claim 1, wherein the heart support system is configured to be inserted into a heart chamber or an aorta by means of a catheter.

16. The heart support system according to claim 1, wherein the at least one contact terminal is configured to connect to the at least one sensor via a sensor line.

17. A method for mounting a heart support system, wherein the heart support system comprises a blood pump, a motor, a motor compartment, at least one sensor disposed on a surface of the blood pump, a sensor line electrically connected to the at least one sensor, and a connection cable, wherein the method comprises:
   providing a motor housing module, the motor housing module comprising:
      a feed-through portion configured to establish an electrical connection between the heart support system and the connection cable; and
      at least one contact terminal, wherein the at least one contact terminal is configured to form a connection between the connection cable and the at least one sensor via an electrical connection external to the motor housing module, wherein the at least one contact terminal has a distal end embedded in a blind hole electrically insulated from the interior of the motor compartment and a proximal end that protrudes proximally beyond the motor housing module, wherein the blind hole is disposed on a side of the motor housing module opposite a pump head of the blood pump; and
   contacting the at least one contact terminal of the motor housing module with the sensor line of the heart support system.

18. The method according to claim 17, further comprising connecting the connection cable of the heart support system to the at least one contact pin of the motor housing module.

19. The method according to claim 17, wherein the at least one contact terminal is configured to connect to a conductor of the connection cable.

20. The method according to claim 17, wherein the at least one contact terminal comprises at least one contact pin.

21. The method according to claim 17, wherein the motor housing module comprises a sensor groove configured to receive the least one sensor.

22. The method according to claim 17, wherein the heart support system further comprising a sensor cap positioned at least partially over the sensor groove and having a measurement window for the at least one sensor.

\* \* \* \* \*